United States Patent
Schmit et al.

(10) Patent No.: US 8,953,171 B1
(45) Date of Patent: Feb. 10, 2015

(54) SIGNAL SECTIONING FOR PROFILING PRINTED-CIRCUIT-BOARD VIAS WITH VERTICAL SCANNING INTERFEROMETRY

(71) Applicants: Joanna Schmit, Tucson, AZ (US); Erik Novak, Tucson, AZ (US)

(72) Inventors: Joanna Schmit, Tucson, AZ (US); Erik Novak, Tucson, AZ (US)

(73) Assignee: Bruker Nano Inc, Santa Barbara, CA (US)

( * ) Notice: Subject to any disclaimer, the term of this patent is extended or adjusted under 35 U.S.C. 154(b) by 121 days.

(21) Appl. No.: 13/719,101

(22) Filed: Dec. 18, 2012

(51) Int. Cl.
*G01B 11/02* (2006.01)
*G01B 11/22* (2006.01)
*G01B 9/02* (2006.01)

(52) U.S. Cl.
CPC ............ *G01B 11/22* (2013.01); *G01B 9/02091* (2013.01)
USPC ........................................................ 356/497

(58) Field of Classification Search
USPC ............ 250/559.01, 559.04, 559.06, 559.16, 250/559.18, 559.19, 559.22, 559.24
See application file for complete search history.

(56) References Cited

U.S. PATENT DOCUMENTS

| | | | | |
|---|---|---|---|---|
| 6,195,168 | B1 * | 2/2001 | De Lega et al. | 356/497 |
| 6,514,597 | B1 * | 2/2003 | Strobel et al. | 428/167 |
| 2001/0042637 | A1 * | 11/2001 | Hirose et al. | 174/255 |
| 2002/0196450 | A1 * | 12/2002 | Olszak et al. | 356/511 |
| 2004/0017563 | A1 * | 1/2004 | James et al. | 356/244 |
| 2004/0131824 | A1 | 7/2004 | Hsieh et al. | |

* cited by examiner

*Primary Examiner* — Tri T Ton
*Assistant Examiner* — Willie Merrell, II
(74) *Attorney, Agent, or Firm* — Antonio R. Durando

(57) ABSTRACT

The bottom surface of a via drilled in a fiber-reinforced PCB is profiled interferometrically with acceptable precision using an objective with sufficiently large numerical aperture to illuminate the bottom under the fibers. The light scattering produced by the inherent roughness of the surface of the via bottom causes diffused light to return to the objective and yield reliable data fringes. Under such appropriate numerical-aperture and surface roughness conditions, the bottom surface of vias can be profiled correctly simply by segmenting the correlograms produced by the scan and processing all fringes that correspond to the bottom surface elevation.

14 Claims, 8 Drawing Sheets

SIGNAL SECTIONING FOR PROFILING PRINTED-CIRCUIT-BOARD VIAS WITH VERTICAL SCANNING INTERFEROMETRY

BACKGROUND OF THE INVENTION

1. Field of the Invention

This invention pertains to the general field of optical metrology. In particular, the invention relates to a method for profiling the bottom surface of vias in printed circuit boards when the view is partially obscured by preferentially oriented reinforcement fibers added to the structure of the boards.

2. Description of the Prior Art

Printed circuit boards (PCBs) are well known structures used in the electronic industry to mount electronic components and connect them to external devices. Printed circuit boards have traditionally been manufactured from fiber layers surrounded by a plastic matrix material. The boards have one or more layers of metalized patterns that, when assembled with the electronic components, form electrical interconnections among them.

In use, assembled PCBs are normally attached to a chassis, such as the frame of a computer, and are therefore subjected to stresses due to vibrations and to forces exerted by the weight of the components attached to them. These forces tend to produce undesirable flexing of the circuit boards with attendant potential loosening of the electrical connections and separation of the electronic components. Therefore, in order to minimize flexing, it has become common practice to reinforce PCBs by means of support structures such as reinforcing bars, beams and rib stiffeners. However, such support structures are often undesirable because they occupy valuable circuit-board surface area, which is contrary to the trend of increasing the density of electrical components on PCBs. Moreover, electrical components are becoming increasingly heavy, thus placing an increased burden on the structure of the PCB.

In addition, ever increasing miniaturization requirements tend to lead to thinner and thinner PCBs, which therefore are also more flexible and more subject to potential damage. U.S. Publication No. 2004/0131824 provides a solution to this problem by reinforcing and stiffening the structure of printed circuit boards in selected locations using preferentially oriented fibers. Selected fibers are removed from the polymeric material matrix of the PCB and replaced with a similar quantity of different-material fibers placed in a predetermined orientation as required to achieve the desired PCB stiffening. Because printed circuit boards tend to flex along a particular axis, the reinforcing fibers are oriented transversely to resist flexure, thereby reducing material fatigue, fracture and failure. FIG. 1 illustrates a section 10 of PCB polymeric matrix where such reinforcing fibers 12 are shown laid cross the structure of the PCB. This reinforcement approach has become common practice in the industry.

During the process of assembly of electronic components to the PCB, holes 14 (referred to as "vias" in the industry) are typically drilled with lasers into the PCB matrix, as shown in FIG. 2, for receiving and soldering the leads or pins of chips and other components. The vias are metalized to form an electrical connection between the electrical component pins inserted into them and the circuit board. Therefore, the vias have to be large and uniform enough to make a good and strong connection between the printed circuit and the electronic components when the vias are filled with soldering material. To that end, knowledge of the exact dimensions of the vias is a critical part of the packaging process and the top and bottom diameters of the vias are measured routinely for quality control purposes.

Various optical systems and techniques are known that could be used to profile vias. These include, without limitation, low-coherence interferometry, confocal microscopy, bright-field and dark-field microscopy (image sharpness techniques), and structured light techniques. These methods are all encompassed by what is generally referred to in the art, interchangeably, as optical metrology, optical profilometry, or 3-D microscopy. The signal captured in low-coherence interferometry (including structured light metrology) is fringes, while in confocal microscopy, bright-field microscopy and dark-field microscopy the optical signal is irradiance.

When the dimensions of the via are measured with low-coherence interferometric (WLI) techniques, the via is scanned with an interferometric objective with a field of view exceeding the top aperture of the via (that is, an objective overlaying the entire via opening or a system adapted to cover that area through stitching of data acquired with high numerical-aperture objective and a smaller field of view) and the top and bottom surfaces are profiled by identifying in conventional manner the scanning heights where local fringe modulation maxima are produced during the scan through focus. However, it has been found that drilling vias in PCBs reinforced with oriented fibers does not produce uniform tubular structures because the reinforcing fiber material tends to melt away at a different rate than the PCB matrix when drilled with a laser and leave behind loose fibers that form a substantially annular shelf 16 that protrudes into the vias 14 (FIG. 2). As a result, the shelf 16 is an impediment to the WLI measurement of the portion of the bottom surface 18 of the via under the shelf because its view is obscured to the overlaying scanning objective 20, as illustrated in FIG. 3.

The conventional approach has been to scan through the height of the via and obtain its dimensions by identifying the position of maximum fringe contrast for each pixel by some method, such as the center of gravity approach. That is, the detector pixels recording light irradiance received from the top surface of the PCB will produce a correlogram with local maximum contrast at corresponding scan positions; the pixels recording irradiance received from the bottom surface of the via visible from the top will produce another correlogram with a local maximum contrast at scan positions corresponding to the bottom; and, similarly, the surface of the fibers constituting the intermediate annular shelf produces a correlogram characterized by well-defined fringes at the scanning positions corresponding to the shelf height. Because the portion of the via's bottom surface below the fiber shelf is obscured to the interferometer's objective by the overlaying shelf, no fringes have been expected to be produced by the bottom regions under the shelf. Therefore, any modulation detected by detector pixels corresponding to these bottom regions of the via has been considered noise and disregarded or treated as insignificant by the algorithms used to profile the bottom of the vias. As a result, the geometry of the bottom surface of vias has been measured based only on the information obtained from detector pixels corresponding to the visible portion of the surface (that is, the portion that is not obscured by the fiber shelf).

It is clear that the conventional approach leads to incorrect measurements because it is known that the bottom of vias is larger than the visible portion inside the inner perimeter of the fiber shelf above it. The present invention provides a simple solution to this problem.

SUMMARY OF THE INVENTION

The invention is based on the discovery that under certain particular conditions the bottom surface of a PCB via can be profiled with acceptable precision using WLI even when its view is obscured by the presence of fibers protruding into the via opening. This is contrary to expectation because scanning interferometry is based on interference between a reference beam and a sample beam reflected from the surface being measured. Therefore, a clear view of the target surface from the objective of the scanning interferometer is always considered essential to a good measurement. However, for the limited purposes of quality-control measurement of vias in fiber-reinforced PCBs, it was found that the bottom of the via can be measured adequately if the conditions are such that sufficient light reaches the bottom surface below the obstructing fibers and is diffusively reflected back to the scanner's objective.

As a first criterion for the invention to work, the numerical aperture of the objective must be sufficiently large to illuminate the portion of the surface under the fibers at the bottom of the via and to allow the reflected light to return to the objective to produce measurement fringes by interfering with the reference beam. Given the typical placement of reinforcing fibers within the matrix of the printed circuit board and the normal extent of their protrusion into the via opening, it was found that a numerical aperture of at least 0.4 in a 20× interferometric objective often provides the necessary angle for the sample beam to illuminate the bottom surface of the via with sufficient reflected light to return to the objective to produce an acceptable measurement.

The roughness of the surface at the bottom of the via is another critical and contributing factor to the effectiveness of the invention. Because surface roughness produces light scattering that in turn results in an effective increase of the ability of reflected light to return to the objective past the shelf of reinforcing fibers, it is important that the bottom surface of the via be sufficiently rough to scatter the reflected light up past the fibers toward the objective. Fortunately, the vias produced by laser drilling tend to have a roughness in the order of a fraction of a micron (typically 300-700 nm), so this factor is inherently present in the applications for which the invention is generally intended.

Under such appropriate numerical aperture of the objective and surface roughness conditions, we discovered that sufficient sample-beam light reaches the area of the bottom surface of the via under the fiber shelf and is diffused back to the objective to enable the measurement of the entire bottom surface simply by processing in its entirety the correlogram corresponding to the bottom surface elevation. That is, rather than discarding as noise the fringes produced at pixels under the shelf of protruding fibers in the via, those fringes are processed as true surface data. Contrary to expectation, we found that surface measurements so conducted lead to materially more precise profiles than previously possible.

Various other features and advantages will become clear from the description of the invention in the specification that follows and from the appended claims. Therefore, to the accomplishment of the objectives described above, this invention consists of the features hereinafter illustrated in the drawings, fully described in the detailed description of the preferred embodiments, and particularly pointed out in the claims. However, such drawings and descriptions disclose only some of the various ways in which the invention may be practiced.

DETAILED DESCRIPTION OF THE INVENTION

As used herein, the term "shelf" refers to the substantially annular structure of reinforcing fibers produced by the process of forming a via in a printed circuit board. As a result of the different materials constituting the reinforcing fibers and the rest of the PCB, the bottom surface of the via includes a correspondingly annular area that is obscured by the overlaying fiber shelf and not directly visible from the top opening of the via. The terms "diffused" and "scattered" and their derivatives are used synonymously.

The invention is described below with reference to low-coherence interferometry (normally referred to in the art also as low-coherence white light interferometry—WLI—or vertical scanning interferometry—VSI). However, it is recognized that it is applicable to any through-focus optical method of measurement. Therefore, for the purposes of claiming the invention, the term "through-focus" is intended to encompass any optical approach whereby an optical signal is captured while a sample surface is passed through the focal point of an objective, such as low-coherence interferometry, confocal, bright-field and dark-field microscopy. In the case of low-coherence interferometry, the optical signal is fringes that yield a process signal referred to as modulation. In the case of confocal microscopy, the optical signal is irradiance that is typically processed as such. In the case of bright-field and dark-field microscopy, the optical signal is irradiance that is normally processed in terms of its standard deviation within neighboring pixels.

Figure 1:
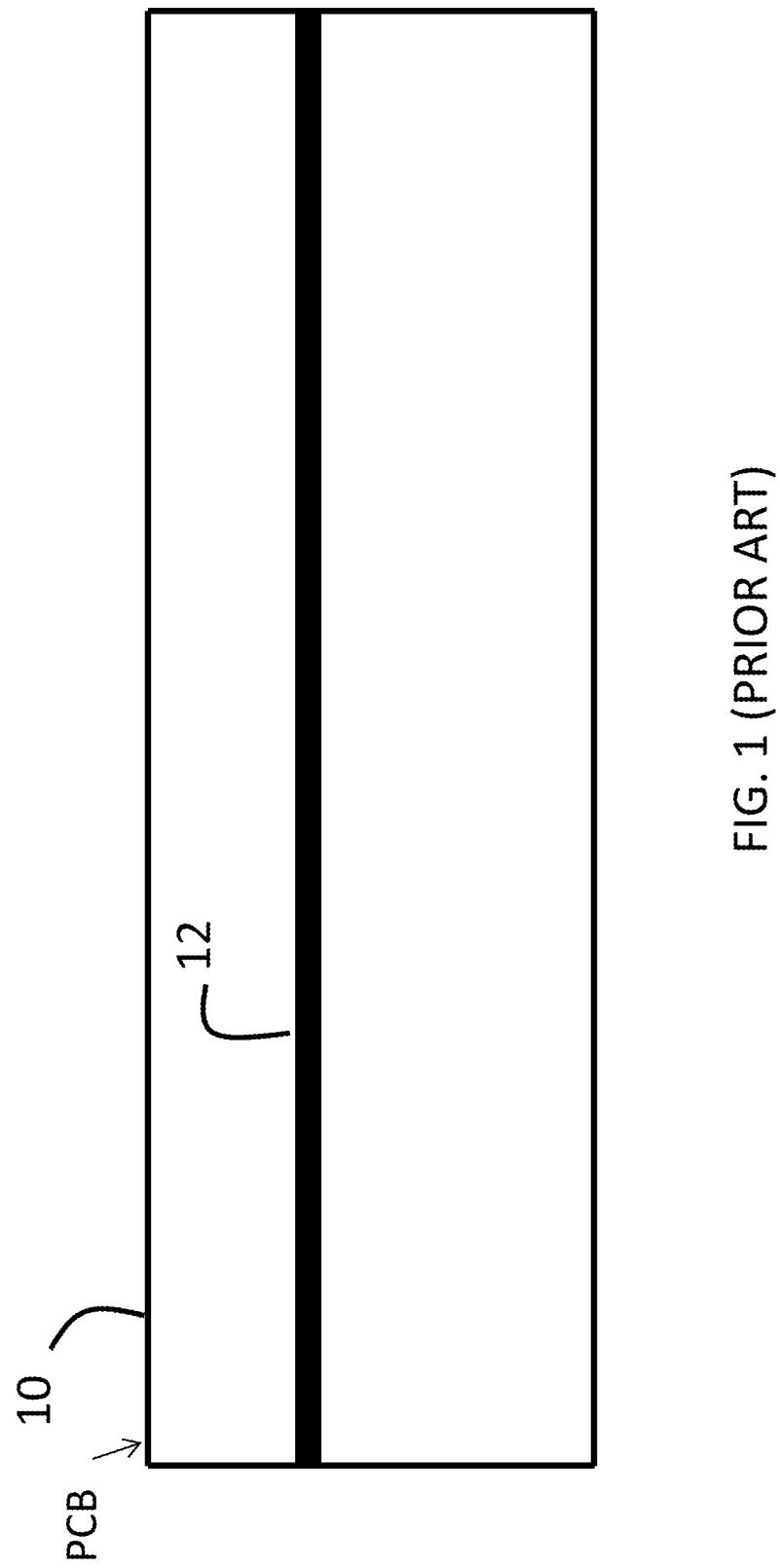
FIG. 1 is an elevational schematic representation of a section of printed circuit board reinforced with a layer of oriented fibers.
Figure 2:
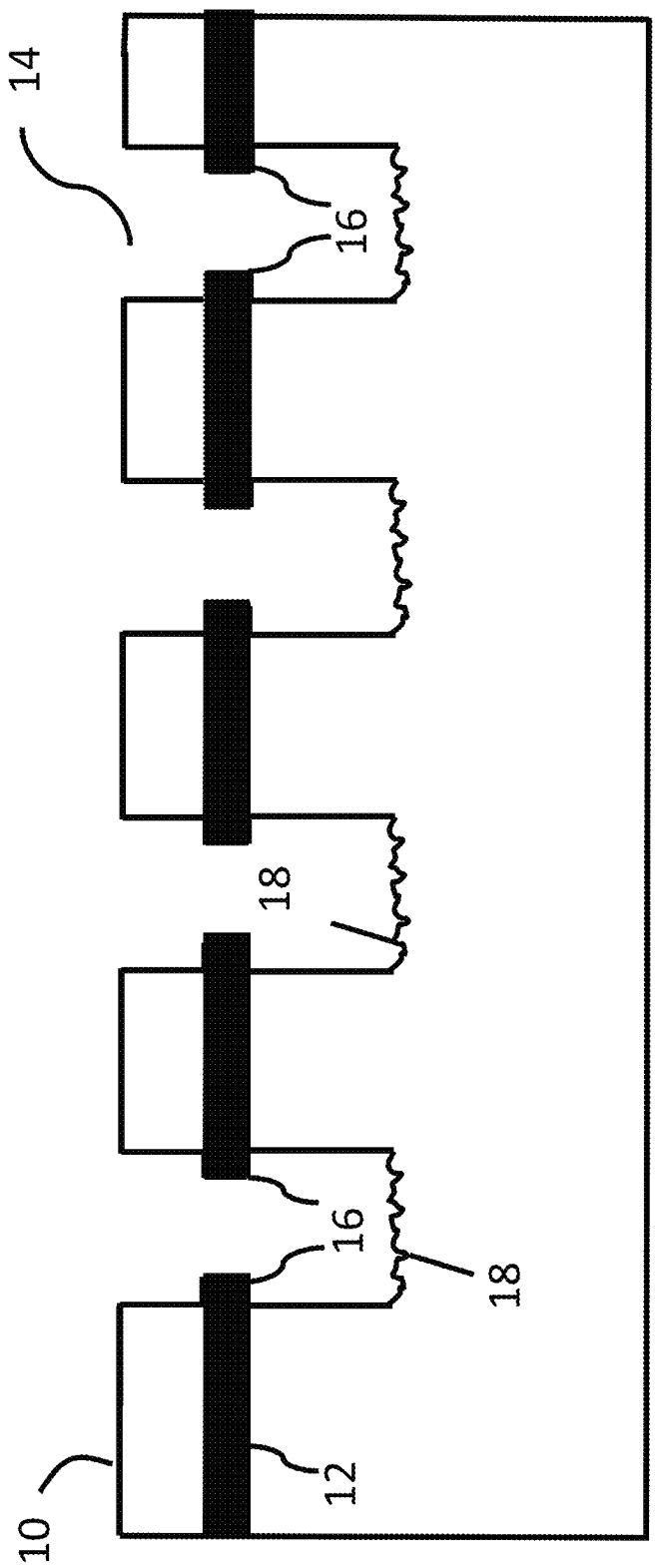
FIG. 2 illustrates vias drilled in the PCB of FIG. 1 and the shelf of fiber residue remaining in each via as a result of a laser drilling operation.
Figure 3:
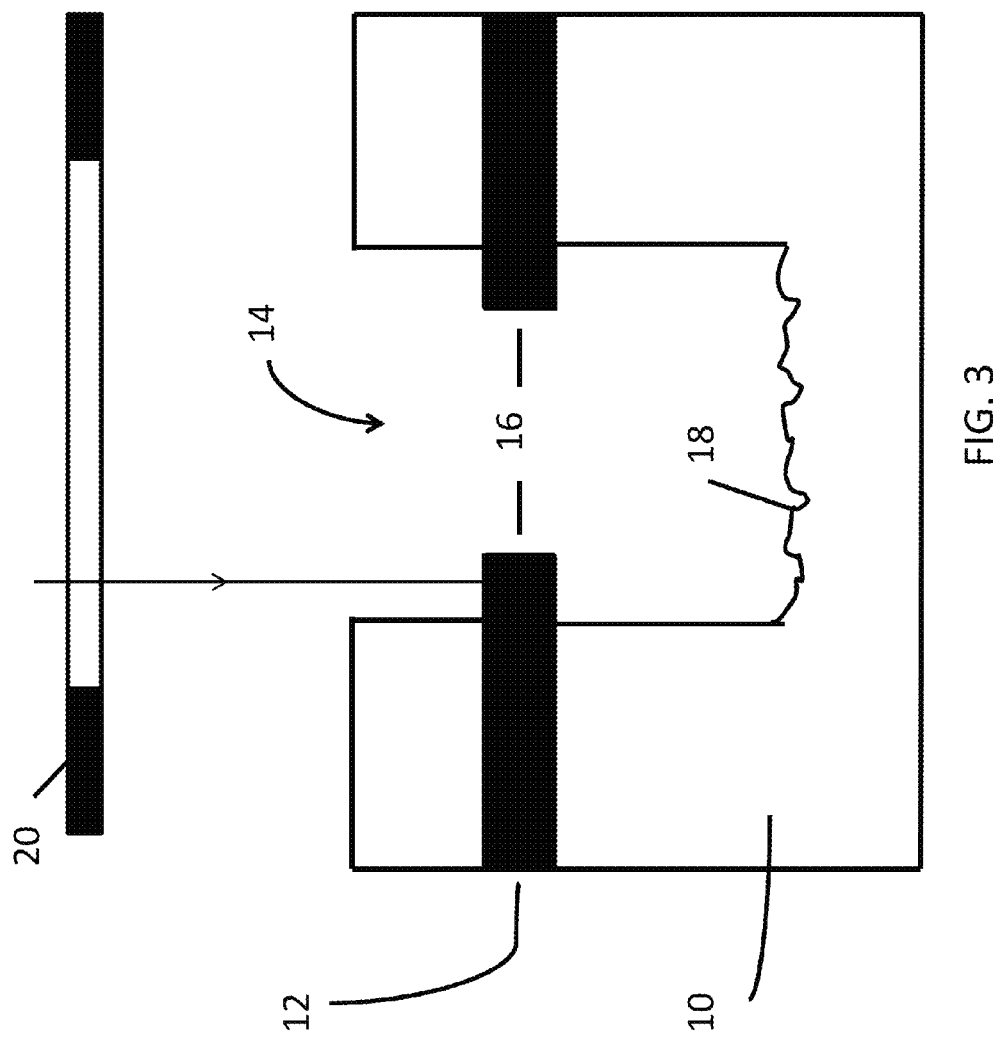
FIG. 3 illustrates the obstruction to WLI illumination provided by the shelf of reinforcing fibers formed by drilling in each via.
Figure 4:
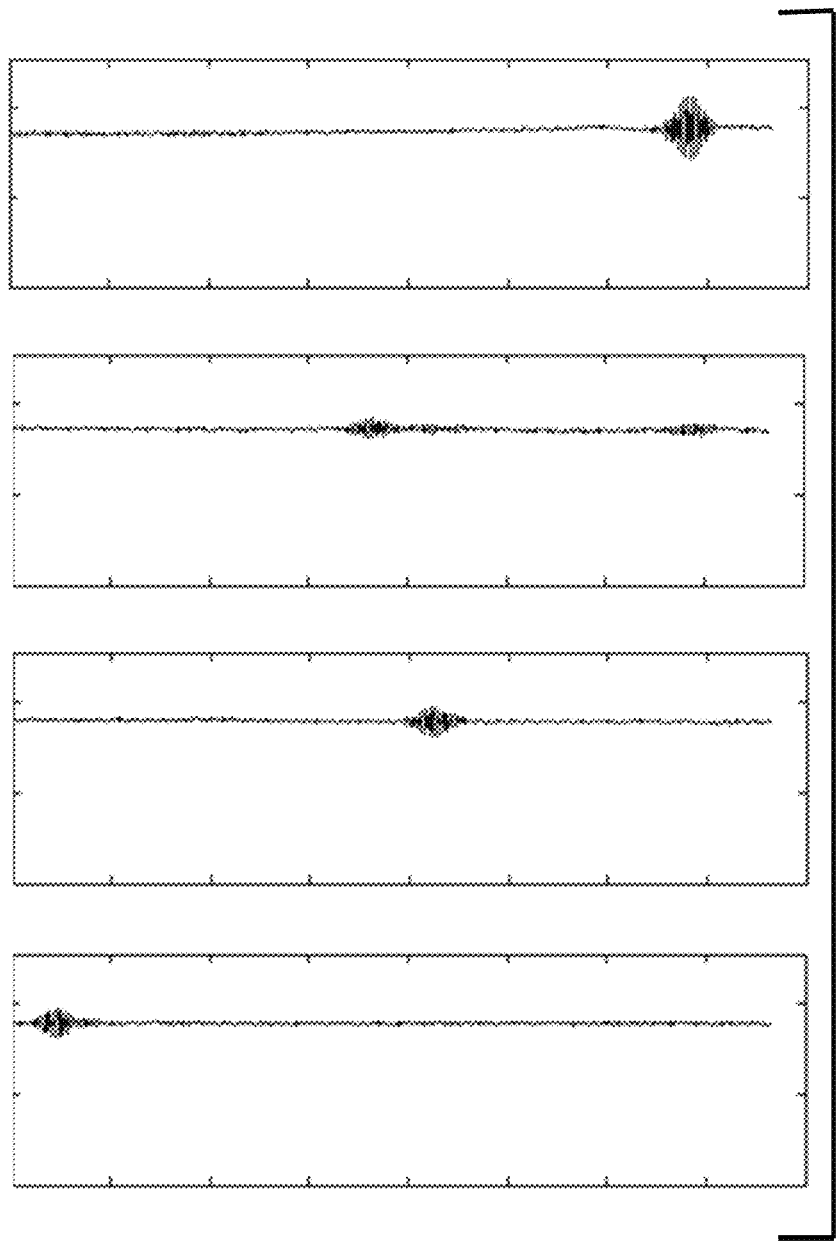
FIG. 4 illustrates four correlograms recorded at four pixels corresponding to the top surface, the intermediate fiber shelf, and the central area of unobscured bottom of a typical PCB via.

FIG. 4 illustrates four correlograms recorded for four pixels corresponding to different areas in the field of view of an interferometric objective scanning a typical PCB via. The first correlogram on the left shows fringes only at the top of the via, thereby contributing to defining the top contour of the opening within the surface of the PCB. As expected, no light goes below the solid surface and no other fringes are produced during the scan. The second and third correlograms correspond, respectively, to a pixel near the via wall overlooking the fiber shelf produced by drilling of the via and to another pixel also over the shelf, but more centrally located away from the via wall. As expected, the pixel over the shelf near the wall (second correlogram) shows a single set of fringes at the height of the shelf because that is the only elevation from which light can be reflected. The third correlogram, on the other hand, shows two sets of local fringes; one at the height of the shelf and another, much smaller, set of fringes below the shelf and near the bottom of the via. This smaller set of local fringes has been discarded in the prior art as noise. The fourth correlogram, on the right of FIG. 4, corresponds to a pixel over the unobstructed bottom of the via. Also as expected, it shows a corresponding single set of fringes at the bottom of the via.

As mentioned, prior-art interferometric procedures routinely discard the bottom set of local fringes (seen in the third correlogram) as noisy data because corresponding to a surface obscured by the fiber shelf overlaying that portion of the bottom surface. As such, algorithms typically reject it using irradiance thresholds designed to isolate and eliminate noise. As a result, the interferometric profile of the via produces an approximately circular top opening, an annular shelf at some depth in the via, and a similarly approximately circular bottom surface corresponding to the inner perimeter of the shelf (i.e., the area directly exposed to the field of view of the scanning objective. Elliptical curves are typically fitted to the data and their major and minor axes are used to define the various shapes for quality-control purposes (for example, the average between the major and minor axes is used as an effective, average diameter of an approximately circular structure).

Figure 5:
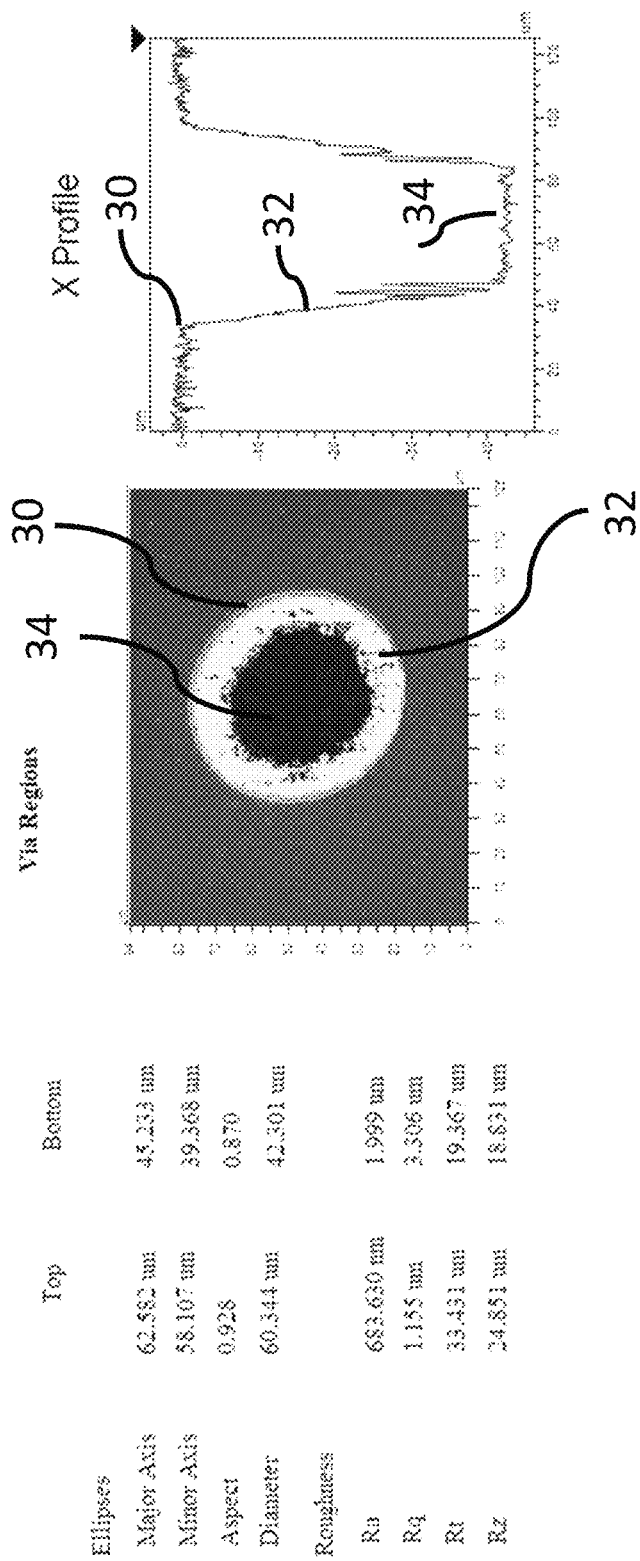
FIG. 5 illustrates the result of a conventional measurement of a PCB via where the approximately circular bottom area is measured to correspond to the inner perimeter of the fiber shelf produced by the laser drilling process.

A typical PCB via is about 20-60 microns deep and has an average diameter of about 40-60 microns. (Average diameter is often used because vias are not perfectly cylindrical.) The fiber shelf created during drilling is about 2-10 microns wide at a depth corresponding to the layer of preferentially oriented reinforcement fibers. FIG. 5 illustrates the conventional measurement result obtained scanning such a via. The measurement produced a via depth of approximately 41 microns, with a top opening 30 with an average diameter of about 60 microns, a fiber shelf 32 about 9-micron wide (i.e., with an average inner-perimeter diameter of about 42 microns) placed about 20 microns from the top, and a correspondingly equal circular bottom area 34 of about 42 microns in average diameter. These results illustrate the fact that this conventional approach to measuring vias interferometrically does not produce a reliable measurement below the shelf 32 because it does not show that the surface of the bottom area 34 extends below the shelf even though that is known to be the case.

Figure 6:
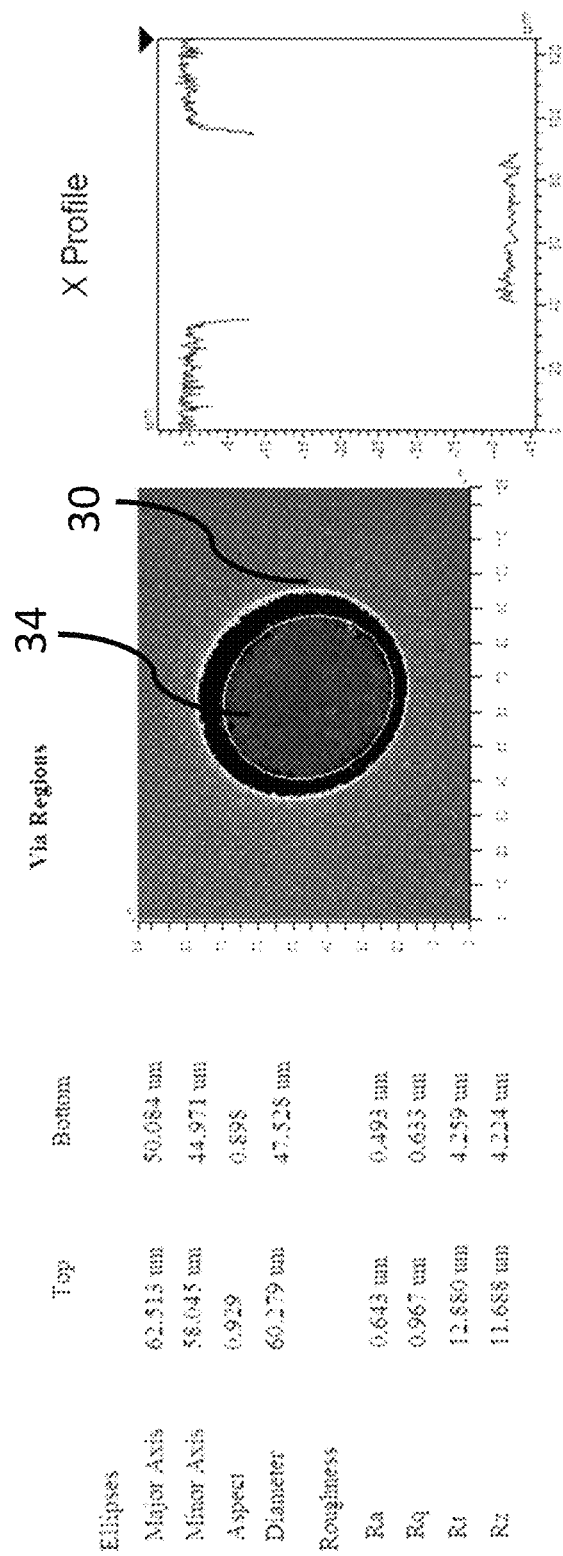
FIG. 6 illustrates the result of a measurement according to the invention of the PCB via of FIG. 5 where the approximately circular bottom area is measured to exceed the inner perimeter of the fiber shelf produced by the laser drilling process and to substantially match the actual size measured by other means.

The essence of the present invention lies in the fortuitous discovery that the data provided by the fringes heretofore considered noise (the bottom fringes of the third correlogram in FIG. 4) can be used advantageously to improve the measurement of the bottom surface of vias. If such data are combined with the correlograms corresponding to the central part of the bottom surface (represented by the fourth correlogram in FIG. 4), the scan of the bottom surface of the via produces a measurement that has been found to represent the actual geometry of the via materially more accurately than believed possible with vertical scanning interferometry. To that end, according to the invention the via is normally scanned from top to bottom (or vice versa) as previously done, but the data are segmented vertically as pertaining to the top region, the shelf region, and the bottom region. The top and shelf regions are profiled as usual, using the fringe data generated by the respective structures during the scan at their respective heights. However, all of the data generated by the bottom structure are used to calculate a profile of the bottom area, including the fringes previously discarded as artifact or noise. FIG. 6 illustrates the results obtained from the interferometric data of FIG. 5 using the segmented approach of the invention. While the area of the opening 30 and the shelf 32 (not shown) remained the same, the surface of the bottom area 34 is measured with an average diameter of about 47 microns, showing that it extends past the 42-micron inner perimeter of the shelf, as expected.

Figure 7:
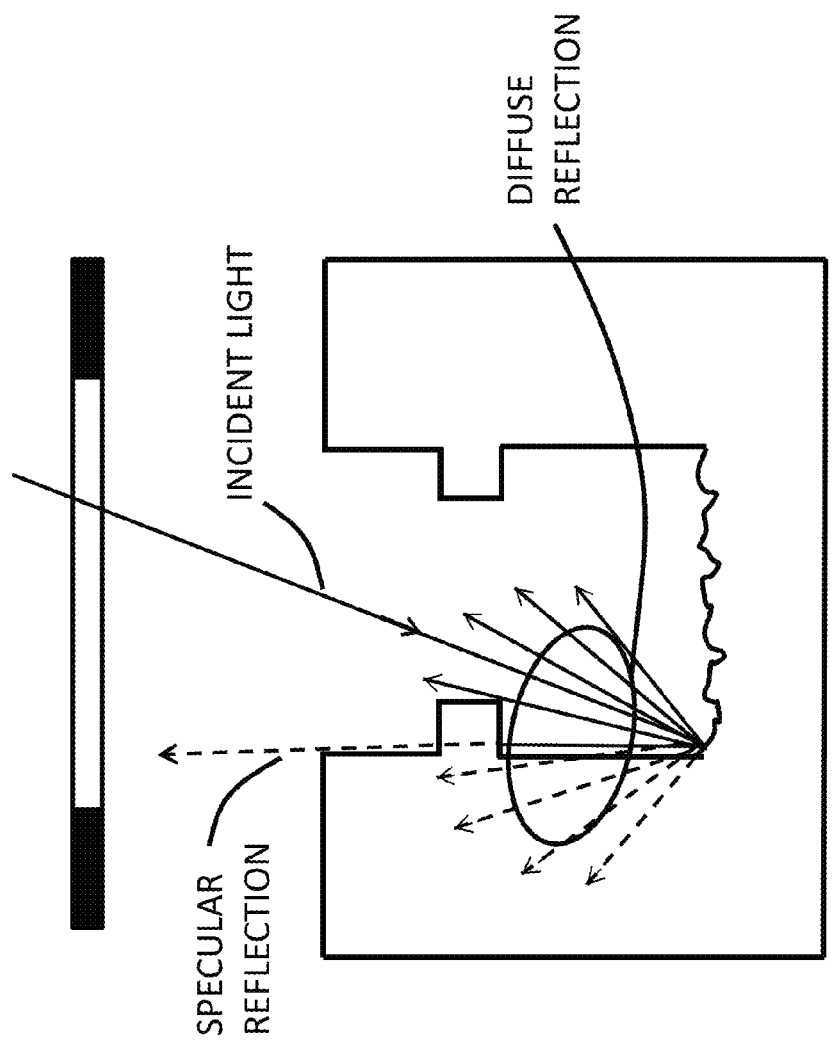
FIG. 7 illustrates the effect of surface roughness on the light returned from the bottom surface of a via for interference with the interferometer's reference beam.

It is believed that this measurement is made possible by light that is scattered off the bottom area 34 from roughness that directs it back to the objective even from incidence locations that do not seem to be accessible to the objective, such that sufficient light is collected, even from below the shelf, to provide meaningful fringe data during the scan. FIG. 7 illustrates such effect on light scattered by roughness in the bottom surface of the via. As mentioned, the vias drilled with a laser beam necessarily have a surface with a degree of roughness sufficient to provide the necessary scatter to reflect light from under the shelf.

Clearly, however, for the invention to work it is above all necessary that some light reach the bottom in areas lying under the shelf. This illumination is achieved by utilizing an objective with a numerical aperture (NA) sufficiently high to guarantee that enough light is projected at an angle below the shelf and diffused back toward the objective to produce measurable fringes. As would be clear to one skilled in the art, the minimum NA suitable for a particular measurement will depend on the exact location of the shelf within the height of the via (and the width of the shelf), but such minimum NA can be easily ascertained empirically or estimated by theoretical calculations. For example, for the via illustrated by the measurements of FIGS. 5 and 6, we found that a NA of at least 0.4 in a 20× interferometric objective was necessary to obtain consistent bottom area results.

Because the measurements of vias for quality-control purposes are performed repeatedly on printed circuit boards having essentially the same structure (with corresponding vias that ideally are also the same and have comparable bottom-surface roughness), the invention is best carried out by first measuring a via using objectives with increasing numerical apertures until the measurement of the bottom area of that particular type of via remains substantially unchanged with increasing NAs greater than a minimum value. That would indicate that in all cases a sufficient amount of light had reached the hidden bottom surface to produce reliable results given the roughness of the via bottom; thus, any of those NAs could then be used with confidence for subsequent measurements of that type of via.

Given the fact that PCB vias are inherently characterized by a sufficiently rough bottom surface (in the order of 300-700 nanometers Ra) following this approach guarantees that the measurements obtained using segmented fringe data according to the invention are reliable and repeatable. In fact, the same via used for the measurements reported in FIGS. 5 and 6 was sectioned mechanically below the shelf and the bottom surface was measured optically under completely open conditions. The measurement produced an average diameter in close agreement with the measurement produced by the segmented approach of the invention (always within 2-3 microns).

Figure 8:
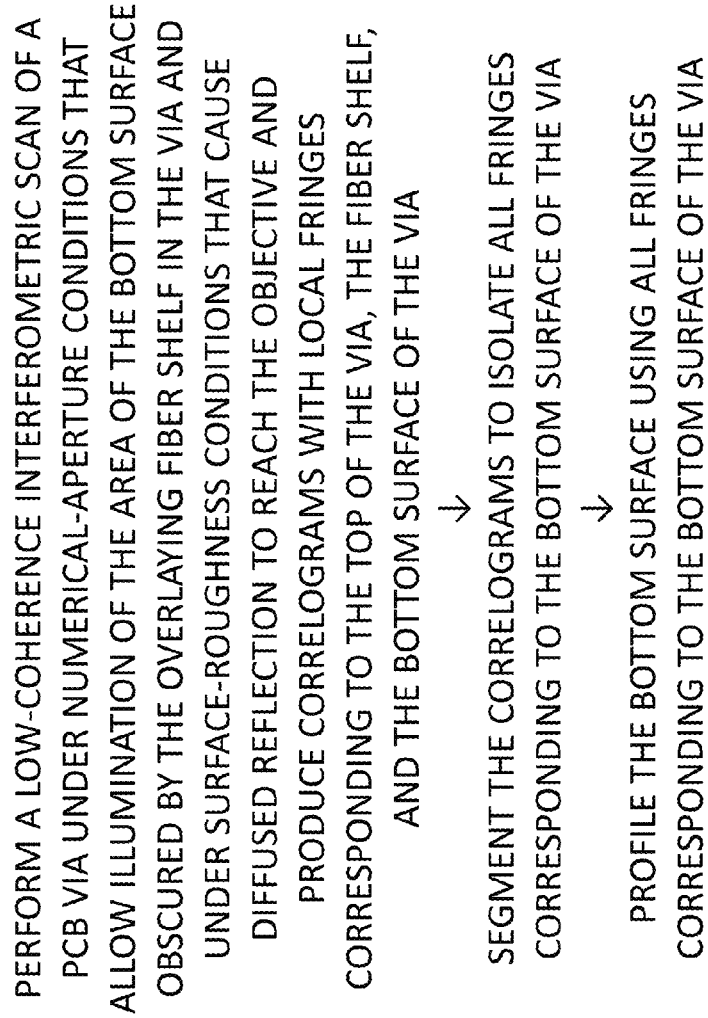
FIG. 8 is a flow-chart of the basic steps of the process of the invention.

Thus, a simple but effective new WLI approach has been disclosed to profile the bottom area of PCB vias formed by drilling the board through a layer of oriented reinforcing fibers. The results have shown to be correct and repeatable so long as a sufficiently large numerical aperture is used in the scanning objective. FIG. 8 is a flow-chart of the basic steps of the process of the invention.

It will be clear to one skilled in the art that the invention may also be practiced by measuring only the bottom of the via; that is, without scanning through the entire height of the via. The invention may also be used to measure any recessed feature having a bottom surface that is partially obscured by an intermediate layer of material placed between the top and the bottom of the feature. Similarly, any surface below and obscured by an overlaying shelf-like layer of material, even if not the bottom surface of a recess, can be measured according to the invention if the surface has the necessary degree of roughness to diffuse light back toward the objective. The same elements of the invention apply to these conditions as well.

Various changes in the details that have been described may be made by those skilled in the art within the principles and scope of the invention herein illustrated and defined in the appended claims. For example, the invention has been described in terms of vias drilled with a laser in the printed circuit board, but it is understood that it could be applied to any via formed by whatever means through an intermediate layer of reinforcing material that partially obscured the bottom of the via. The recessed feature does not have to be round, but it could have any geometry compatible with an intermediate layer of material partially obscuring the bottom of the feature. It could be a longitudinal trench where the bottom has been formed by undercutting the top layer. Also, any through-focus based method (such as interferometric, confocal, bright-field, and dark-field) using a high numerical aperture objective for shape measurement is expected to benefit from the invention because the same conditions of high NA and bottom surface roughness would cause the light to reach under the shelf and be partially scattered back to the objective, thereby providing information about the surface under the shelf. Thus, while the invention has been shown and described in what are believed to be the most practical and preferred embodiments, it is recognized that departures can be made therefrom within the scope of the invention, which is not to be limited to the details disclosed herein but is to be accorded the full scope of the claims so as to embrace any and all equivalent apparatus and methods.

What is claimed is:

1. An interferometric method of measuring a bottom surface of a via containing an overlaying shelf resulting from drilling the via through a layer of reinforcing material in a printed circuit board, said shelf obscuring a portion of the bottom surface of the via, the method comprising the following steps:
    performing a low-coherence scan of the via to produce correlograms with local fringes corresponding respectively to a top opening of the via, to the shelf, and to the bottom surface of the via;
    segmenting said correlograms to isolate fringes corresponding to the bottom surface of the via including fringes corresponding to a portion of the bottom surface obscured by said overlaying shelf in the via; and
    profiling the bottom surface using said fringes corresponding to the portion of the bottom surface obscured by the overlaying shelf in the via;
    wherein said performing step is carried out with an objective having a numerical aperture and with said bottom surface of the via having a roughness so that an illuminating beam produces a diffusive reflection from said portion of the bottom surface of the via obscured by the shelf and said diffusive reflection is directed back to the objective.

2. The method of claim 1, wherein said performing step includes identifying a numerical aperture of the objective such that said portion of the bottom surface of the via obscured by the intermediate layer of material is illuminated by said illuminating beam.

3. The method of claim 1, wherein said numerical aperture is at least 0.4 in a 20× interferometric objective.

4. The method of claim 1, wherein said overlaying shelf results from laser drilling the via in the printed circuit board.

5. The method of claim 4, wherein said bottom surface of the via has a roughness of at least 300 nanometers Ra.

6. The method of claim 5, wherein said numerical aperture is at least 0.4 in a 20× interferometric objective.

7. The method of claim 1, further including the step of calculating an average diameter of the via.

8. An interferometric method of measuring the bottom surface of a via containing an overlaying fiber shelf resulting from drilling the via through a layer of oriented reinforcing fibers in a printed circuit board, said method comprising the following steps:
    performing a low-coherence scan of the via to produce correlograms with fringes corresponding to the bottom surface of the via; said performing step being carried out with an objective having a numerical aperture and with said bottom surface of the via having a roughness so that an illuminating beam produces a diffusive reflection from a portion of the bottom surface of the via obscured by the overlaying fiber shelf and said diffusive reflection is directed back to the objective; and
    profiling the bottom surface using said fringes corresponding to the portion of the bottom surface of the via obscured by the overlaying fiber shelf.

9. The method of claim 8, wherein said performing step includes identifying a numerical aperture of the objective such that said portion of the bottom surface of the via obscured by the intermediate layer of material is illuminated by said illuminating beam.

10. The method of claim 8, wherein said numerical aperture is at least 0.4 in a 20× interferometric objective.

11. The method of claim 8, wherein said overlaying shelf results from laser drilling the via in the printed circuit board.

12. The method of claim 11, wherein said bottom surface of the via has a roughness of at least 300 nanometers Ra.

13. The method of claim 12, wherein said numerical aperture is at least 0.4 in a 20× interferometric objective.

14. The method of claim 8, further including the step of calculating an average diameter of the via.

* * * * *